United States Patent [19]
Graham

[11] Patent Number: 6,075,028
[45] Date of Patent: Jun. 13, 2000

[54] METHOD OF TREATING TOURETTE'S SYNDROME AND RELATED CNS DISORDERS

[76] Inventor: Richard Graham, 1879 County Rd. 10, Ancram, N.Y. 12502

[21] Appl. No.: 09/401,302

[22] Filed: Sep. 23, 1999

[51] Int. Cl.⁷ .................................................. A61K 31/505
[52] U.S. Cl. ............................................................. 514/258
[58] Field of Search ............................................. 514/258

[56] References Cited

U.S. PATENT DOCUMENTS

| | | | |
|---|---|---|---|
| 5,250,534 | 10/1993 | Bell et al. ................................ | 514/258 |
| 5,670,539 | 9/1997 | Richardson .............................. | 514/567 |
| 5,955,611 | 9/1999 | Dunn et al. .............................. | 544/262 |

*Primary Examiner*—Raymond Henley, III
*Attorney, Agent, or Firm*—Kubovcik & Kubovcik

[57] ABSTRACT

A method for treating Tourette's Syndrome and other central nervous system disorders. An effective amount of sildenafil or a pharmaceutically acceptable salt thereof is orally administered to patients suffering from Tourette's Syndrome and other central nervous system disorders to diminish the symptoms associated with such a disorder.

5 Claims, No Drawings

METHOD OF TREATING TOURETTE'S SYNDROME AND RELATED CNS DISORDERS

BACKGROUND OF THE INVENTION

1. Field of the Invention

The present invention relates to a method of treating Tourette's syndrome and other related central nervous system (CNS) disorders.

2. Description of Related Art

Tourette's Syndrome (TS) is an autosomal dominant neuropsychiatric disorder characterized by a range of neurological and behavioral symptoms. Typical symptoms include (I) the onset of the disorder before the age of 21 years, (ii) multiple motor and phonic tics although not necessarily concurrent, (iii) variance in the clinical phenomenology of the tics, and (iv) occurrence of quasi daily tics throughout a period of time exceeding one year.

Motor tics generally include eye blinking, head jerking, shoulder shrugging and facial grimacing. Phonic or vocal tics include throat clearing, sniffling, yelping, tongue clicking and uttering words out of context.

The pathophysiology of TS is currently unknown. However, it is believed that neurotransmission dysfunction is implicated with the disorder. Diseases that are often associated with or accompany TS include Attention Deficit Disorder with or without Hyperactivity, obsessive or compulsive behaviors, learning disabilities, and behavior and sleep problems. Other CNS disorders commonly associated with neurotransmission dysfunction and, particularly, cholinergic deficiency include presenile dementia (early onset of Alzheimer's disease), senile dementia (dementia of the Alzheimer's type), Huntington's chorea, tardive dyskinesia, hyperkinesia and mania.

Current treatment for TS mostly includes the administration of medications which are prescribed for neurotransmitter (i.e., choline, dopamine, adrenerine, and serotonin) disorders, including haloperidol, pimozide, clonidine, clonazepam, and nitrazepam. Compounds that modulate the activity of various receptors have been suggested as treatment due to a decreased number of receptors (particularly acetylcholine (Cosford et al., U.S. Pat. No. 5,686,473) and $D_2$ dopamine receptors (Kerrigan et al., U.S. Pat. No. 5,767,116)) in the brains of patients suffering CNS disorders. Additionally, nicotine pharmacology has been suggested in suppressing TS. (Bencherif et al., U.S. Pat. No. 5,731,314). It has also been suggested that TS is caused by the supply of tryptophan to the brain, and TS symptoms have been treated by increasing and decreasing tryptophan supply to the brain. (Richardson, U.S. Pat. No. 5,670,539) It has also been suggested that treatment with nitric oxide synthase inhibitors in dopaminergic systems to reduce the amount of nitric oxide in the brain is useful in reducing the symptoms of TS.

Stimulants such as methylphenidate and dextroamphetamine may be prescribed for hyperactivity and Attention Deficit Disorder, but often increase the tics of Tourette's syndrome. Fluoxetine and clomipramine are often prescribed to relieve obsessive and compulsive symptoms. Other side affects from medication can include fatigue, motor restlessness, weight gain, social withdrawal, depression, cognitive impairment, and impotence. Thus, there is a continuing search in this field of art for improved methods for relieving the symptoms of TS and the associated afflictions without the side affects.

SUMMARY OF THE PRESENT INVENTION

The present invention is a new method for treating TS and other CNS disorders. The method consists of the oral administration of an effective amount of sildenafil or a salt thereof to patients suffering from TS and other CNS disorders to diminish the symptoms associated with the CNS disorder.

DETAILED DESCRIPTION OF THE INVENTION

The present invention is a method for treating the symptoms associated with central nervous system disorders by the administration of an effective amount of sildenafil or a salt thereof to effectively diminish the symptoms associated with the CNS disorder.

Sildenafil citrate, commonly known as Viagra® available from Pfizer, Inc., is commonly known for the treatment of erectile dysfunction. Sildenafil citrate is a selective inhibitor of cyclic guanosine monophosphate (cGMP) specific phosphodiesterase type 5 (PDE5). By inhibiting PDE5, sildenafil enhances the normal physiological action of nitric oxide activation of the enzyme guanylate cyclase, which results in locally increased levels of cGMP and smooth muscle relaxation.

Sildenafil is 1-[4-ethoxy-3-(6,7-dihydro-1-methyl-7-oxo-3-propyl-1H-pyrazolo[4,3-d]pyrimidin-5-yl)phenylsulphonyl]-4-methylpiperazine. Sildenafil has the molecular formula: $C_{22}H_{30}N_6O_4S$. Its molecular weight is 474.6. Sildenafil and its pharmaceutically acceptable salts are described in U.S. Pat. No. 5,250,534, entitled "Pyrazolopyrimidinone Antianginal Agents", the disclosure of which is hereby incorporated by reference.

Although the generic name sildenafil represents a free base, the present invention is also meant to encompass its pharmaceutically acceptable salts, such as hydrochloride, hydrobromide, hydroiodide, nitrate, sulfate, bisulfate, phosphate, acid phosphate, acetate, lactate, citrate, acid citrate, tartrate, bitartrate, salicylate, succinate, maleate, gluconate, methane sulfate, ethane sulfate, methane sulfonate (mesylate), benzenesulfonate (besylate), toluene sulfonate and p-toluenesulfonate salts. Most preferably, the salt form is sildenafil citrate.

It is believed that any administration of sildenafil or a salt thereof found effective in relieving the symptoms associated with CNS disorders may be used. Preferably, a sildenafil salt is dispensed in an oral tablet form.

Sildenafil or its salt is administered in an amount and at a frequency that is effective in relieving the symptoms of CNS disorders. Preferably, the compound is administered in single dosages on a daily basis starting with smaller doses, about 25 mg, and increasing the amount daily until the majority of symptoms subside, usually up to about 100 mg. Most preferably, about 50 mg of sildenafil citrate is administered daily.

EXAMPLE

A male patient suffering from TS was prescribed clonidine to control the twitching and tic that are common symptoms of TS. One of the side affects of clonidine is impotency. Under a physicians care, the patient then suspended taking the clonidine and began taking a 50 mg dose of sildenafil citrate daily. No clonidine was taken while sildenafil citrate was taken. Upon the second day of taking sildenafil citrate, the patient's twitching and other symptoms of TS gradually dissipated. The relief from the symptoms lasted approximately 16 hours. The symptoms gradually returned over the last several hours of said 16 hour period as the effects of the drug diminished.

The drug was administered in three trials. Trial 1 lasted for 3 days, Trial 2 lasted for 4 days, and Trial 3 lasted for 6 days. On each occasion, the patient's symptoms abated on the second day after taking the pill until they disappeared completely. On each occasion, the symptoms returned as the use of the drug ended.

The patient also suffered from Attention Deficit Disorder, commonly associated with TS. He found that, while taking the sildenafil citrate, his head cleared, he was able to focus, and he was not as easily distracted as he was when he was not medicated.

This invention provides a method of treating symptoms of TS and CNS disorders by the administration of the compound sildenafil in an amount sufficient to provide relief of such symptoms without producing the side effects commonly associated with other forms of treatment.

It should be understood that the invention is not limited to the particular example described herein, but that various changes and modifications may be made without department from the spirit and scope of this novel concept as defined in the follow claims.

What is claimed:

1. A method of treating the symptoms of a central nervous system disorder in a human being, which comprises administering to said human being an effective amount for treating said central nervous system disorder of 1-[4-ethoxy-3-(6,7-dihydro-1-methyl-7-oxo-3-propyl-1H-pyrazolo[4,3-d]pyrimidin-5-yl)phenylsulphonyl]-4-methylpiperazine or a pharmaceutically acceptable salt thereof.

2. The method of treating a central nervous system disorder of claim 1, wherein said central nervous system disorder is Tourette's syndrome.

3. The method of treating a central nervous system disorder of claim 1, wherein the compound is a citrate salt.

4. The method of treating a central nervous system disorder of claim 1, wherein the compound is administered orally.

5. The method of treating a central nervous system disorder of claim 1, wherein a dosage amount is about 25 to about 100 mg per day.

* * * * *